United States Patent
Melker et al.

(10) Patent No.: US 10,368,807 B2
(45) Date of Patent: Aug. 6, 2019

(54) FUSION OF DATA FROM MULTIPLE SOURCES FOR NON-INVASIVE DETECTION OF RESPIRATORY PARAMETERS

(71) Applicant: XHALE ASSURANCE, INC., Gainesville, FL (US)

(72) Inventors: Richard J. Melker, Gainesville, FL (US); Sean Cohen, Gainesville, FL (US); Huwei Tan, Gainesville, FL (US)

(73) Assignee: XHALE ASSURANCE, INC., Gainesville, FL (US)

( * ) Notice: Subject to any disclaimer, the term of this patent is extended or adjusted under 35 U.S.C. 154(b) by 930 days.

(21) Appl. No.: 14/512,425

(22) Filed: Oct. 11, 2014

(65) Prior Publication Data

US 2015/0105632 A1 Apr. 16, 2015

Related U.S. Application Data

(60) Provisional application No. 61/889,582, filed on Oct. 11, 2013.

(51) Int. Cl.
| | | |
|---|---|---|
| *A61B 5/00* | (2006.01) | |
| *A61B 5/08* | (2006.01) | |
| *A61B 5/083* | (2006.01) | |
| *A61B 5/0205* | (2006.01) | |
| *A61B 5/1455* | (2006.01) | |

(52) U.S. Cl.
CPC .......... *A61B 5/7246* (2013.01); *A61B 5/0205* (2013.01); *A61B 5/0816* (2013.01); *A61B 5/0826* (2013.01); *A61B 5/0836* (2013.01); *A61B 5/14551* (2013.01); *A61B 5/6819* (2013.01)

(58) Field of Classification Search
CPC .................................................. A61B 5/7246
See application file for complete search history.

(56) References Cited

U.S. PATENT DOCUMENTS

| | | | |
|---|---|---|---|
| 7,318,808 B2 * | 1/2008 | Tarassenko | A61B 5/0816 600/529 |
| 7,690,378 B1 * | 4/2010 | Turcott | A61B 5/0816 128/201.23 |
| 8,430,817 B1 * | 4/2013 | Al-Ali | A61B 5/7221 128/920 |
| 8,740,806 B2 * | 6/2014 | Parfenova | A61B 5/4818 600/484 |
| 9,011,347 B2 | 4/2015 | Addison | |
| 9,095,307 B2 * | 8/2015 | Parfenova | A61B 5/4818 |
| 2008/0066753 A1 | 3/2008 | Martin | |
| 2010/0298730 A1 * | 11/2010 | Tarassenko | A61B 5/0816 600/529 |

(Continued)

OTHER PUBLICATIONS

A. Johansson, "Neural network for photoplethysmographic respiratory rate monitoring", Medical & Biological Engineering & Computing, Jun. 2003.

*Primary Examiner* — John R Downey

(57) ABSTRACT

Provided herein are methods and systems for validating and interpreting respiratory signals in order to provide comprehensive non-invasive methods to monitor patients at risk for respiratory depression and apnea. In the present invention, data from multiple respiratory monitoring technologies (or from multiple channels of one monitoring technology) is fused so that the patient's true respiratory state may be elucidated.

6 Claims, 2 Drawing Sheets

(56) References Cited

U.S. PATENT DOCUMENTS

| | | | |
|---|---|---|---|
| 2010/0312075 A1* | 12/2010 | McGonigle | A61B 5/0816 600/301 |
| 2010/0331715 A1 | 12/2010 | Addison | |
| 2011/0004081 A1 | 1/2011 | Addison | |
| 2012/0160243 A1 | 6/2012 | Berthon-Jones | |
| 2012/0165623 A1 | 6/2012 | Lynn | |
| 2013/0172759 A1* | 7/2013 | Melker | A61M 15/0066 600/476 |
| 2014/0275938 A1* | 9/2014 | Addison | A61B 5/0873 600/407 |
| 2015/0038810 A1* | 2/2015 | Melker | A61B 5/0295 600/323 |

\* cited by examiner

FUSION OF DATA FROM MULTIPLE SOURCES FOR NON-INVASIVE DETECTION OF RESPIRATORY PARAMETERS

CROSS-REFERENCE TO RELATED APPLICATIONS

This application claims the benefit of U.S. Provisional Application No. 61/889,582, filed Oct. 11, 2013, the contents of which are incorporated herein by reference in their entirety.

FIELD OF THE INVENTION

The present invention relates to biological sensors, and in particular, to photoplethysmography sensors. The present invention also relates to processing and analysis of data from biological sensors.

BACKGROUND OF THE INVENTION

There is a critical unmet need in the field of medicine for non-invasive measurement of respiratory parameters in spontaneously breathing patients. Presently, most respiratory medical equipment is used for the long-term monitoring of patients receiving mechanical ventilation. Because most mechanically ventilated patients are intubated, many respiratory parameters can be precisely measured in a way not possible with non-intubated patients. These parameters include those obtained from capnometry, including end tidal $CO_2$ [$EtCO_2$] and $CO_2$ waveform measurements, tidal volume ($V_T$), airway pressure ($P_{aw}$), minute ventilation ($V_E$), respiratory rate (RR), respiratory effort/work of breathing (RE/WOB), inspiratory:expiratory (I:E) ratio, and dead space measurements.

Thus, while patients in the OR and ICU may receive intensive respiratory monitoring, similarly reliable monitoring is not presently available for non-intubated patients who are often ambulatory, such as those on general care floors and other areas of the hospital. Numerous organizations including the FDA, ASA and APSF have noted this lack of monitoring to be problematic and are calling for new technological advances to migrate intensive respiratory monitoring to non-intubated patients. There is also a critical need for improved monitoring of patients receiving patient controlled anesthesia (PCA) since opioids frequently lead to respiratory depression and subsequent morbidity or mortality. Efforts to identify patients likely to suffer respiratory depression or arrest in a preemptive manner have been only partially successful and adequate monitoring solutions are still lacking even if such patients are identified.

Polysomnography (PSG) is a method of monitoring patients for the evaluation of sleep apnea. PSG uses non-invasive technology but much of it cannot be readily adapted for monitoring patients in the hospital because it is cumbersome and costly. Further, while PSG may be effective in determining if a patient has sleep apnea and further categorizing what type of sleep apnea (central v. obstructive), it is not used for real-time continuous monitoring to detect respiratory events. Polysomnographs must be read by trained technicians or physicians and analysis may be very time consuming and so PSG does not lend itself to continuous non-invasive monitoring of ambulatory patients.

SUMMARY OF EMBODIMENTS OF THE INVENTION

Provided according to embodiments of the invention are methods of determining the respiratory status of an individual that include monitoring a PPG waveform from a PPG sensor secured to a central source site of an individual over time; monitoring a waveform indicative of nasal air flow of the individual; comparing a portion of the PPG waveform with a corresponding portion of the waveform indicative of nasal airflow; and determining a respiratory parameter or condition based on the similarity and/or differences between the PPG waveform and the waveform indicative of nasal airflow. In some embodiments, the respiratory parameter is respiration rate. In some cases, the reported respiration rate is the respiration rate based on the PPG waveform if the respiration rate based on the PPG waveform is substantially the same as the respiration rate based on the waveform indicative of nasal airflow.

Also provided according to embodiments of the invention are arbiter systems configured to compare a portion of the PPG waveform with a corresponding portion of the waveform indicative of nasal airflow (and/or $CO_2$ flow from an individual's nose); and determine a respiratory parameter or condition based on the similarity and/or differences between the PPG waveform and the waveform indicative of nasal airflow (and/or $CO_2$ flow from the individual's nose).

Further provided according to embodiments of the invention are respiration monitoring systems for a patient that include a processor configured to process data from a primary respiration sensor to calculate a respiratory parameter of the patient; determine a statistical confidence in the respiratory parameter; and if the statistical confidence is below a predetermined limit, (1) process additional data from the primary respiration sensor and recalculate the respiratory parameter; and/or (2) calculate the respiratory parameter from data from a secondary respiration sensor.

BRIEF DESCRIPTION OF THE DRAWINGS

The following drawings are provided to illustrate various aspects of the present inventive concept and are not intended to limit the scope of the present invention unless specified herein.

DETAILED DESCRIPTION OF EMBODIMENTS OF THE INVENTION

Figure 1:
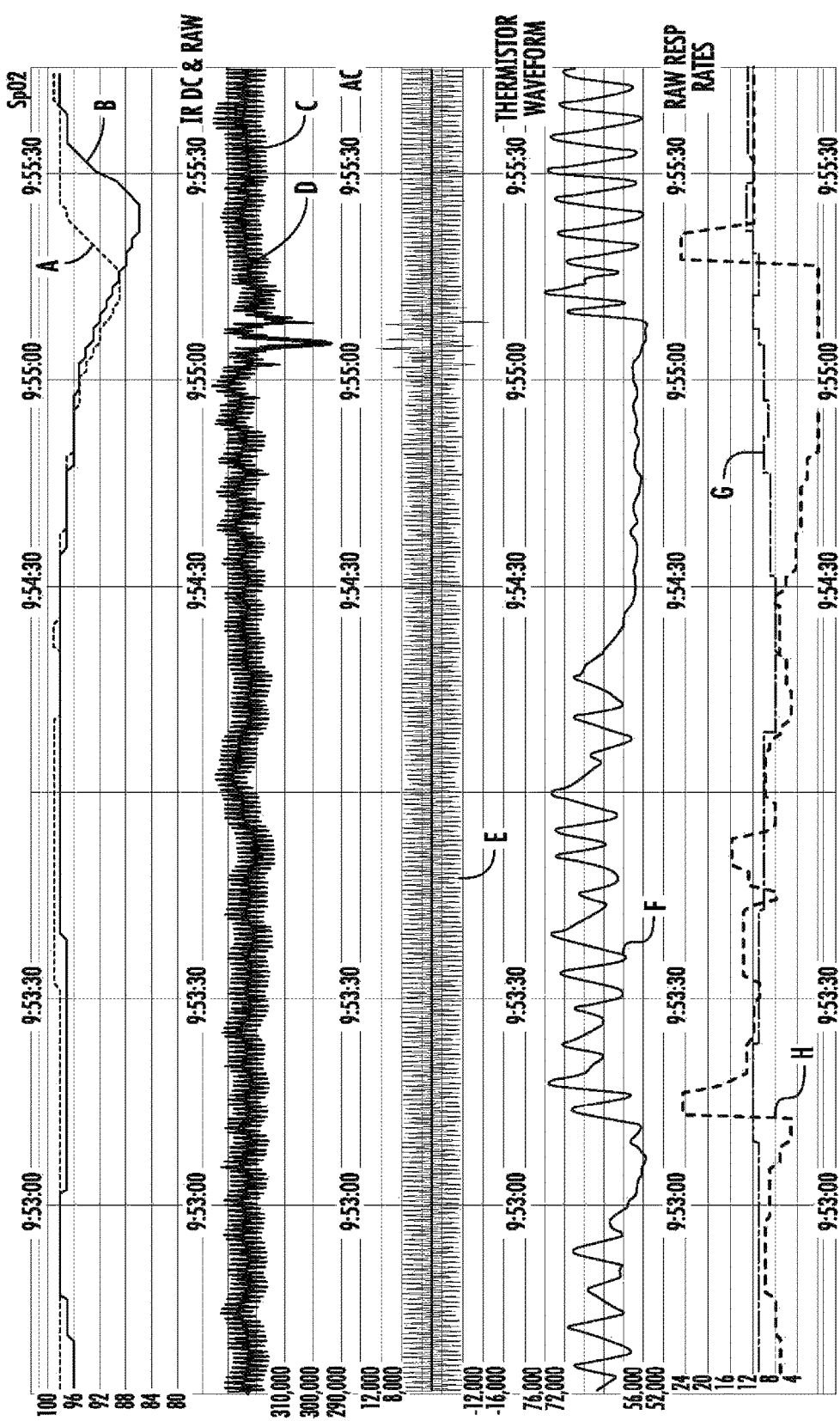
FIG. 1 provides PPG, thermistor and capnometry data over time for a patient in the operating room who is having periods of obstructive apnea typical of obstructive sleep apnea. Signals "A" and "B" show the blood oxygen saturation (SpO2) over time obtained from a patient's nasal alar and finger, respectively. The signal "C" is the raw PPG signal, while signal "D" is the processed DC component of the PPG signal. Signal "E" is the AC component signal. Signal "F" is the thermistor signal (nasal air flow) over time. Signal "G" is the capnometry signal over time and signal "H" is the respiration rate over time as determined by the processed AC component of the PPG signal.

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element is referred to as being "on" or "adjacent" to another element, it can be directly on or directly adjacent to the other element or intervening elements may also be present. In contrast, when an element is referred to as being "directly on" or "directly adjacent" to another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers refer to like elements throughout the specification.

It will be understood that, although the terms first, second, etc. may be used herein to describe various elements, these elements should not be limited by these terms. These terms are only used to distinguish one element from another. Thus, a first element discussed below could be termed a second element without departing from the teachings of the present invention.

The present inventors have discovered methods and systems for validating and interpreting respiratory signals in order to provide comprehensive non-invasive methods to monitor patients at risk for respiratory depression and apnea. In the present invention, data from multiple respiratory monitoring technologies (or from multiple channels of one monitoring technology) is fused so that the patient's true respiratory state may be elucidated. Examples of respiratory monitoring sensors that may be used in embodiments described herein include, but are not limited to:

(1) nasal air flow monitors (e.g., a thermistor), which can provide respiratory parameters including, but not limited to, respiration rate (RR) and absence or respiration (apnea), and depth of breathing, a surrogate for tidal volume ($V_T$);

(2) photoplethysmography (PPG), which can provide parameters including, but not limited to, respiratory rate (RR), respiratory effort (RE), ratio of inspiration to expiration (I:E ratio) and blood oxygen saturation ($S_pO_2$);

(3) capnometry, which can provide respiratory parameters including, but not limited to, those described above; and (4) acoustic respiratory monitoring.

Other respiratory monitoring technologies may also be used in some embodiments. Using a signal processor, fusing two or more physiological signals obtained from the sensors above can allow for a primary signal(s) to be "validated" in order to determine when the signals can be relied upon and when they cannot. In addition, two or more of these signals can be input into the processor's arbiter function, which may determine how to handle parameter reporting and alarms. The processor's arbiter is defined as the fusion point of all sensor data, whereby the arbiter may compute data quality and/or assign weights to particular data or parameters for the purpose of selecting or calculating reported parameters and alarm qualification.

According to some embodiments of the present invention, provided are methods and systems for determining and/or validating the accuracy of respiratory parameters by processing and comparing the PPG waveform (e.g., amplitude or area under the curve of a signal over time) or respiratory parameter determined therefrom with waveforms (or respiratory parameters determined therefrom) from at least one additional respiration detector. For example, a processor may compare the PPG waveform, or a parameter determined therefrom, with a waveform or a respiratory parameter determined from a nasal flow detector (e.g., a thermistor), carbon dioxide detector (capnometer) and/or an acoustic respiration sensor. By fusing the data from the various respiration monitors, a picture of the actual physiology occurring with the individual may be better assessed, as the processor's comparison of the different waveforms may determine whether particular signals are due to patient physiology or artifacts that without validation may lead to false alarms. In general, the processor fuses data from two or more different respiration sensors, but in particular cases, only a PPG sensor is needed because validation can occur by fusing data obtained from different components of the PPG signal. For example, respiratory parameters determined by the AC and DC component streams of the PPG signal may be fused, and in some cases, the blood oxygen saturation measurements (also obtained from the PPG signal) may also be evaluated by the processor's arbiter to decide whether an alarm should be generated.

Photoplethysmography (PPG)

PPG is commonly used for the determination of blood oxygen saturation ($S_pO_2$). This is termed pulse oximetry and is based on the absorption characteristics of red and IR light at different hemoglobin saturations. Because the path length of the light is not fixed, the "ratio of ratios" of the AC and DC components of the two wavelengths is used to calculate $S_pO_2$. In "classic" oxygen saturation measurements, it is assumed that the important information is contained in the "AC" component of the PPG signal and that the DC is only used to determine the "offset" of the signal from the baseline.

The inventors have determined that both the AC and DC components of the PPG signal, when measured at the nasal alae or other central source sites (those sites above the neck, e.g., columella, nasal septum, over the ophthalmic artery) contain valuable respiratory parameter information which is unavailable from conventional digit-based PPG measurements. For instance, the inventors have previously have focused on the separation of the AC and DC components to determine respiratory rate (RR), respiratory effort (RE), ratio of inspiration to expiration (I:E ratio). Separation of the AC and DC components may be achieved by a number of different methods, but in some embodiments, the components are separated as discussed in U.S. Pat. No. 8,529,459. In some embodiments, the DC component signal is determined by interpolating the peaks and interpolating the troughs of the combined signal (e.g., a raw signal), and then averaging the two interpolated lines (interpolated peak line and interpolated trough line) to form the DC component signal waveform. The AC component signal may be obtained by subtracting the DC component signal waveform from the combined signal, which in some cases may be the raw signal, but in other cases the combined signal may be a signal that has been filtered or processed.

The amplitude or area under the curve of the AC component waveform may vary with changes in blood volume reflecting the effects of intrathoracic pressure changes throughout the respiratory cycle on differential volume in the right and left ventricle and therefore the carotid arteries. Evaluating these changes may provide the respiratory rate, respiratory effort and evidence of airway obstruction (AO). In particular cases, a specific PPG waveform pattern ("sawtooth" pattern") may reflect intermittent increased respiratory effort with air movement (snoring). Research has demonstrated that the PPG signal from central source sites can reliably detect RR, RE and I:E ratio while signals from the digits are too damped to provide the needed signal resolution. Body position and the degree of AO both affect the amplitude of the AC PPG signal. For instance, because more blood is present in the head when patients are reclining (prone or supine) or in a head down position, the PPG signal (amplitude) is larger and determination of RR and AO is easier.

The DC signal is likewised influenced by intrathoracic pressure changes and body position. Larger AC amplitudes may lead to a larger DC signal and increased tidal volume and AO may lead to larger amplitude of the DC signal. The DC signal may also be valuable in determining respiratory effort and I:E ratios. Evaluating the amplitudes or area under the curves for the AC and DC signals may allow for precise determination of RR and apnea and relative changes in RE, $V_T$, AO and I:E ratios.

The AC and the DC components may be used to determine respiration rate and respiratory effort, and a processor's analysis regarding whether a breath has occurred may use one or both of the AC and DC components of the PPG waveform. As the amplitudes of the signal may change upon inspiration or expiration, the processor may use a zero cross method to determine whether a breath has occurred. In some embodiments, the processor uses a "band cross" method, such that a range of amplitudes centered around a zero crossing point may be assigned to the signal, and the size of the band may be determined, for example as fixed amplitude band or as a percentage of the total signal amplitude. In such cases, the processor may determine that a breath occurred when the PPG signal crosses the band of amplitudes. This is analogous to the zero point crossing method but instead of a single point, the signal must cross the amplitude band for a breath to have been deemed to occur. This decreases the likelihood that noise in the signal will affect the respiration rate. Once the signal crosses the amplitude band, the processor may determine whether the signal crossing is statistically valid (e.g., run a T-test) and if not, the processor may then evaluate an additional data point and/or the data may be fused with other component (AC or DC) signals or respiration signals from other sensors to assess the validity of the measurement.

Nasal Air Flow Monitoring

There may be instances where the PPG signal is of relatively small amplitude (e.g., in some cases, when patients are sitting or standing and breathing with minimal effort) and having other parameters to supplement the PPG signals is valuable. One reliable means to monitor respiratory parameters is by airflow or temperature changes detected at the nostril. For example, during inspiration, a thermistor placed at the nostril detects a relative decrease in temperature compared to exhalation since, in most situations, body temperature, and therefore exhaled breath temperature, is higher than ambient temperature. Thus, detection of changes in temperature is often a suitable means in evaluating respiration, and thus, respiration rate. Further, since the changes in temperature are also related to tidal volume ($V_T$), thermistor amplitude can be used to determine the relative $V_T$. Furthermore, lack of a thermistor signal after a reliable signal is a good indication of apnea. Data from a nasal airflow monitor (from one or both nostrils) may be monitored and compared with the PPG waveform.

In some embodiments, the respiratory data from the nasal airflow detector may be handled analogously to the PPG data. As the amplitudes of the signal may change upon inspiration or expiration, the processor may use a zero cross method to determine whether a breath has occurred. In some embodiments, the processor may use a "band cross" method such that a range of amplitudes centered around a zero crossing point may be assigned to the signal, and the size of the band may be determined, for example as fixed amplitude band or as a percentage of the total signal amplitude. In such cases, the processor determines whether a breath occurred (based on the nasal airflow detector) when the signal crosses the band of amplitudes. This decreases the likelihood that noise in the signal will affect the respiration rate. Once the signal crosses the amplitude band, the algorithm may determine (e.g., run a T-test) whether the signal crossing is statistically valid and if not, additional data may be evaluated and/or the data may be fused with respiratory parameters obtained from the PPG signal or other respiration monitors to assess the validity of the measurement.

Capnometry

As mention previously, capnometry may provide respiratory parameters such as end tidal $CO_2$ [$etCO_2$] and $CO_2$ waveform measurements, tidal volume ($V_T$), airway pressure ($P_{aw}$), minute ventilation ($V_E$), respiratory rate (RR), respiratory effort/work of breathing (RE/WOB), inspiratory: expiratory (I:E) ratio, and dead space measurements. Such parameters may generally be reliably used for monitoring adequacy of ventilation if the patient is intubated. Unfortunately both hyper- and hypoventilation may cause low $etCO_2$ measurements in non-intubated patients, while hypoventilation may cause an increase in $etCO_2$ in intubated patients. Capnometry is generally considered a monitoring standard but is often believed to be unreliable by anesthesia providers. In many instances of capnometry monitoring in non-intubated patients, the monitor will indicate no breathing, when in fact the patient is breathing normally. Likewise, while capnometry is valuable in determining the adequacy of ventilation in intubated patients, it provides no information about airway obstruction or other indicators of respiratory depression seen with opioids. Because of the frequent failure of capnometry in spontaneously breathing patients, anesthesia providers may ignore the capnometer and place a cannula on the patient merely to receive insurance reimbursement for a procedure since capnometry monitoring is required by many insurance companies.

The inventors have determined that the reliability of capnometry can be ascertained by combining data from the capnometer with data from one or more of the other sensors described herein. If the RR from the capnometer is equal to the RR determined by the above techniques, it is likely that the capnometer is performing correctly. If the RR from the capnometer is erratic while the RR determined from the PPG sensor (and/or air flow detector) is steady, the anesthesia provider should question the veracity of the capnometry measurements. Numerous studies have shown that capnometry is reliable at detecting RR at best, and that the capnograms and etCO$_2$ displays cannot be relied upon. However if the capnograms mirrors the air flow or PPG waveforms, it is likely that the capnograms are reliable.

In some embodiments, the respiratory data from the capnometer may be handled analogously to that from the PPG and nasal airflow sensors. As the amplitudes of the signal may change upon inspiration or expiration, the processor may use a zero cross method to determine whether a breath has occurred. In some embodiments, the processor uses a "band cross" method such that a range of amplitudes centered around a zero crossing point may be assigned to the signal, and the size of the band may be determined, for example as fixed amplitude band or as a percentage of the total signal amplitude. In such cases, the processor determines that a breath occurred when the signal crosses the band of amplitudes. This decreases the likelihood that noise in the signal will affect the respiration rate. Once the signal crosses the amplitude band, the processor may then determine (e.g., run a T-test) whether the signal crossing is statistically valid and if not, the additional data may be evaluated and/or the data may be fused with respiratory parameters obtained from other respiration monitors to assess the validity of the measurement.

Other Monitors

Data from other respiration monitors may also be compared and/or fused with PPG, thermistor and/or capnometer measurements. For example, as discussed above, an acoustic respiration monitor may also be used. In particular embodiments, the processor may further evaluate data from other sensors to determine respiratory rate, respiratory effort, apnea or any other respiratory parameter. For example, data from one or more of accelerometers, ECG, PSG, EKG, and the like, may also be evaluated by the processor's arbiter to more fully determine the physiological state of the patient.

Analysis of Multiple Signals to Determine or Validate Respiratory Parameters

By fusing and/or comparing data from multiple signal streams/sensors, additional information regarding the physiological status of the patient may be ascertained. Such information may used by a processor's arbiter to determine when alarms or other actions should be effected.

In some embodiments of the invention, methods of determining the respiratory status of an individual include monitoring a PPG waveform from a PPG sensor secured to a central source site of an individual over time; monitoring a waveform indicative of nasal air flow of the individual; comparing a portion of the PPG waveform with a corresponding portion of the waveform indicative of nasal airflow; and determining a respiratory parameter or condition based on the similarity and/or differences between the PPG waveform and the waveform indicative of nasal airflow. For example, if both the PPG waveform and the waveform from the nasal airflow sensor indicate a breath, the arbiter in the processor may report that a breath occurred. If they do not agree, the arbiter may determine the quality of each data input, and report a breath if a predefined confidence level is achieved. The processor may further wait for additional data points before reporting a respiratory parameter. The respiratory data obtained from the PPG sensor may also be compared to one or more additional/alternative sensors to validate the respiratory parameters from the PPG sensor.

The following examples describe some of additional ways comparing or fusing data from multiple channels or sensors may provide new information or methods of monitoring respiration.

1. Determination of Central Vs. Obstructive Apnea

Determination of obstructive from central apnea may be determined by using data from both air flow and PPG sensors. Obstructive apnea typically shows no flow at the thermistor (no air flow from the nose) but increased amplitude of the DC PPG signal due to attempts to breathe against an obstructed airway. Severe obstruction can show changes in the AC component as well. Central apnea may be characterized by lack of both air flow and DC evidence of respiratory efforts. Many instances of obstructive breathing without apnea are characterized by a air flow measurement combined with sawtooth (ramping upward followed by sharp decrease in amplitude) AC component and/or DC component waveforms of increased amplitude indicative of obstructive but effective breathing such as snoring. The processor's arbiter may evaluate data (waveforms) both the PPG and flow sensors to differentiate between when a patient is snoring, when a more serious obstruction is occurring and when a central apnea is occurring. For example, the processor may evaluate an increase in amplitude of a DC component signal over time, and at the same time assess a thermistor's waveform. Particular predefined limits in signal amplitudes or frequencies may be programmed into the processor so that if particular signals or signal combinations occur, alarms may be sounded. For example, if the thermistor's waveform shows a decrease or cessation of air flow (by a predefined amount or percentage), while the PPG signal's DC component signal increases to a predefined amplitude or by a predefined percentage (or meets a certain criteria for indicating a problematic trend), the processor may be programmed to thus initiate an alarm.

2. Blood Oxygen Saturation for Validation of Respiratory Parameters

It been observed that desaturation measured by the S$_P$O$_2$ is often seen with apneic events but not with obstructive breathing (snoring). However, when obstruction is significant enough to lead to apnea or little if any air movement, desaturations are always present. Thus, the combination of pulse oximetry with derived parameters from the PPG (and in some cases air flow and/or capnometry measurements) can be used to provide a comprehensive picture of the respiratory status of a patient. In particular examples, an accelerometer may also be used to provide information regarding patient movement and body position. If signal quality is poor due to movement, it is unlikely that the patient is suffering significant respiratory compromise and the signals can be largely ignored (for short durations) if the oxygen saturation remains normal. In fact, even short periods of difficulty with signal processing (poor signal) may be ignored or given less importance if the oxygen saturation of the patient remains normal. Typically, these periods should be of short duration (e.g., <20-30 seconds), but the reassurance of adequate oxygen saturation, especially in patients breathing room air, mitigates the need to sound alarms (false positives), a major cause of failure to respond in a timely manner to true (true positive) alarms. Likewise, detection of significant hypoxia/desaturation in the presence of what are believe to be adequate respiratory patterns, should be prioritized and an alarm sounded as there are few instances where desaturation occurs in the absence of respiratory decompensation. Thus, in addition to providing far more reliable respiratory information in a timely manner, the combination of the above technologies should significantly decrease the number of false alarms that lead to alarm fatigue and fail to recognize a true emergent situation.

Thus, in some embodiments, a processor evaluates respiratory data from a PPG sensor (and/or any other respiration sensor) to evaluate respiratory rate, respiratory effort and/or any other respiratory parameter. The processor also evaluates the $S_pO_2$ at the same time. When an arbiter in the processor determines that a suspect respiratory event is occurring (as described above), it may evaluates the $S_pO_2$ and if the $S_pO_2$ is above a predetermined level, it may wait a predetermined time, or wait for further measurements, before sounding an alarm. Additionally, if an accelerometer is used, the arbiter may evaluate input from the accelerometer in determining whether to sound an alarm. If movement and $S_pO_2$ values are below a predefined value, or follow a particular trend, then the arbiter may effectuate an alarm.

3. Mini-Desaturations

The inventors have also recently discovered that patients may have frequent "mini-desaturations" which are defined as a drop in the $S_pO_2$ of >3% but less than >10% of the baseline $S_pO_2$. These mini-desaturations have been correlated with PPG changes indicative of partial airway obstruction and produce PPG patterns similar to the sawtooth pattern described above. Increased frequency of mini-desaturations per hour correlated with increased severity of partial airway obstruction. Thus, by monitoring both the $S_pO_2$ and PPG signals, trends can be observed that can detect more serious degrees of obstruction and decreased $S_pO_2$ before they occur. By monitoring the number of mini-desaturations per hour and the PPG signals it would be unnecessary to alarm with each episode, but if the episodes increase in frequency (greater than some predefined frequency) and/or the $S_pO_2$ and PPG demonstrate progressive declines and increasing obstruction respectively, an alarm would sound indicating the patient needs a higher degree of monitoring and observation.

Thus, in some embodiments, the arbiter of a processor evaluates inputs from both the PPG signal directly (AC and/or DC components) and/or inputs from another respiratory sensor to evaluate respiratory rate and respiratory effort over time, and further evaluates the number of mini-desaturations per a defined time period. If the respiratory rate reaches a predefined upper or lower limit, the respiratory effort is above a predefined limit and/or the number or mini-desaturations reaches a predefined limit, then an alarm may be initiated. The arbiter may have a set value of different limits (based on a number of different respiratory parameter) that suggests a problematic trend, and may evaluate the data (based on inputted upper and/or lower limits for different respiratory parameters) to determine whether an alarm should sound.

4. Determination of Effective Respiratory Efforts

The ability to determine effective respiratory efforts from ineffective ones may be extremely important. The use of PPG parameters combined with air flow (e.g., thermistor) and/or capnometry data, allows the unique ability to determine the total number of respiratory EFFORTS v. the number of EFFECTIVE respiratory efforts (contributing to effective ventilation). An effective respiratory effort is one which leads to the exchange of oxygen and carbon dioxide. Ineffective respiratory efforts result in movement of deadspace or no airflow at all thus lack effective gas exchange. By combining the PPG signal with the thermistor and/or the capnogram it can be determined whether the respiratory efforts are effective or not. Again, the trends of the PPG and thermistor and/or capnometry will demonstrate specific patterns when a patient transitions from effective respiratory effort to ineffective ones.

For instance, a patient may be breathing spontaneously with adequate tidal volume to have effective gas exchange. At a later point in time, medication may be administered and/or the patient may fall asleep. At such time, the PPG amplitude (and area under the curve) may fall while the thermistor shows smaller breaths. Similar changes may be seen on the capnogram, but in general capnometry is unreliable in spontaneously breathing patients. The respiratory patterns seen with the PPG and thermistor are similar to those seen during sleep studies with polysomnography. The use of PPG plus the thermistor can characterize obstructive apnea from central apnea. With obstructive apnea, the PPG demonstrates respiratory efforts, but the thermistor shows no air movement. With central apnea, both the PPG signal and the thermistor lack evidence of attempts to breath.

Further, there is increased interest in sleep medicine in respiratory event related arousals (RERA). By combining the PPG and thermistor signals it is easy to detect RERAs because the criteria for diagnosing RERAs include desaturation and arousals. After a period of apnea or hypopnea, the PPG shows a characteristic increase in amplitude and area under the curve as the patient arouses from hypoventilation. Knowledge of desaturation in addition to PPG and thermistor parameters is helpful in determining whether the patient is in acute distress and an alarm needs to be initiated, or whether trends in fused data can be followed. In addition, there may be a significant period of both effective and ineffective efforts without a concomitant desaturation. The instant invention, by fusing data from a number of sensors, will allow a greater degree of certainty of the respiratory status of a patient while using only a limited number of sensors. Further, since the ratio of respiratory effort v. effective respiratory effort can change over time, certain trends are likely to be indicative of pending respiratory compromise/failure (more efforts with less effective ventilation) and may lead to earlier detection of pending decompensation in time to intervene before morbidity or mortality.

In a particular embodiment, distinguishing ventilation from respiratory effort is accomplished by comparing the respiration rate from the PPG signals with respiration rate derived from the thermistor. When these rates agree (within a predetermined tolerance), ventilation is considered successful (an effective respiratory effort). When these rates diverge such as when the thermistor respiration rate decreases sufficiently relative to the PPG respiration rate, then the patient may be considered apneic or hypopneic to the point of non-ventilation. In some cases, if this divergence lasts longer than a predetermined time period, e.g., 20-30 seconds (the length of time for defined apnea), and the saturation has declined, an alarm is generated. However, if no desaturation is observed with the apnea event, then an error message may be generated.

A processor may use signals derived from a combination of photoplethysmography (PPG) and an air flow detector (e.g., a thermistor) placed in the path of respiratory flow to calculate respiratory rate (RR) and the ratio successful ventilations to respiratory efforts (RE). This algorithm may use multivariate analysis to filter and demodulate physiological signals from the sensors to provide information on the desired parameters. Such an algorithm is useful for generating alarms to predict respiratory depression, apnea, hypopnea, and other breathing disorders. In one embodiment, the processor would report the respiratory rate as the number of breaths resulting in sufficient gas exchange for respiration while also reporting the ratio to, or the number of respiratory efforts made. The current quality and trending quality of the input signals may also be measured. One measure of signal quality is the signal to noise ratio (SNR). By monitoring the SNR and establishing a trend of "normal"

signal amplitude, an alarm can be set if the SNR ratio decreases below a threshold determined to reflect the point of adequate ventilation.

Methods of Data Fusion

In some embodiments of the invention, the processor may fuse multiple channels statistically in frequency and time domains for providing precise and robust respiratory parameters of interest. In some embodiments, the processor may use at least one of mathematics, applied statistics and Bayesian method, Chemometrics and multivariate methods, pattern recognition and classification methods, and adaptive blind signal process, and the like, to abstract the desired independent components from the multiple channels.

In particular embodiments, in a first step, raw signals are processed into intermediate components that are treated as inputs. This includes the PPG signal being separated into the pulsatile AC component and the venous DC component and also calculating the oxygen saturation (SaO2). The logic is contained in the arbiter, where specific rules are programmed to provide reliable outputs from the input channels.

In some embodiments, the processor may use several layers of data validation intended to filter out artifacts and non-respiratory components of the raw and intermediate signals. One such filter measures the Inspiratory to Expiratory ratio (I:E ratio) of a breath. When a trend of I:E ratio is established, it can be used to cancel out false peaks in the respiratory signals. As an example, if a patient breaths with I:E ratio of 1:2, and two breaths are detected within a time less than double the average inspiratory time, than the detection is likely the result of an artifact or irregular breathing pattern. It is the goals of this data validation and filtering to provide the most accurate inputs possible to the arbiter for creating reportable parameters.

As described above, inspiration and expiration may be evaluated by a zero point or band pass crossing method. As the amplitudes of the signal may change upon inspiration or expiration, a zero cross method may be used to determine whether a breath has occurred. In some embodiments, a "band cross" method may be used such that a range of amplitudes centered around a zero crossing point may be assigned to the signal, and the size of the band may be determined, for example as fixed amplitude band or as a percentage of the total signal amplitude. In such cases, a breath is determined to have occurred when the signal crosses the band of amplitudes. This decreases the likelihood that noise in the signal will affect the respiration rate. Once the signal crosses the amplitude band, the processor may run a T-test to validate whether the signal crossing is statistically valid and if not, the algorithm may then be iterated.

For a particular sensor, if the T-test shows that the signal is not sufficiently valid (the confidence level is not acceptable), then data fusion may or may not occur within the arbiter depending on other conditions being met. The same potential breath may be evaluated with the other sensors and T-Tests may be performed, and the algorithm evaluates whether a breath occurred based on the calculated confidence of the data obtained from respiratory sensor and channel (e.g., can compare and evaluate both AC and DC components to determine respiration rate). Blood oxygen saturation and other physiological parameters may also be evaluated by the processor to assess whether a breath occurred or whether indeterminate respiration is acceptable. For example, if it is not clear whether a breath or series of breaths had occurred based on the PPG and other respiration sensors, but the blood oxygen saturation does not decrease, then the algorithm may allow for a lag period before sounding an alarm because the patient is sufficiently oxygenated.

Systems for Processing Data from Multiple Channels/Sensors

Provided according to some embodiments of the invention are systems that may perform the methods described herein. As described herein, a processor (which may include one, two or more individual processors associated therewith) may process data, evaluate data, calculate parameters and include the arbiter to determine when an alarm may be effectuated. Any suitable processing machine, microprocessor, computer or signal processing device may be used. In some embodiments, the processor is connected to an internal bus. Microprocessors may be adapted to execute software, which may include an operating system and one or more applications, as part of performing the functions described herein. Also connected to the bus may be a read-only memory (ROM), a random access memory (RAM), user inputs, display, and speaker. RAM and ROM are illustrated by way of example, and not limitation. Any suitable computer-readable media may be used in the system for data storage. Computer-readable media are capable of storing information that can be interpreted by microprocessor. This information may be data or may take the form of computer-executable instructions, such as software applications, that cause the microprocessor to perform certain functions and/or computer-implemented methods, such as AC and DC separation, data fusion and arbiter function. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

The systems may also include one or more of the sensors described herein, and in some cases, may include a monitor for visualization of the data. The systems may also include an oxygen delivery apparatus, such that under certain circumstances, oxygen may be delivered to the patient, either manually after an alarm, or in a closed-loop system, whereby the arbiter may determine that conditions are such that oxygen is automatically administered. In some cases, a patient may wear a cannula but no oxygen is delivered unless and until the system determines that the individual is undergoing an adverse respiratory event and needs oxygen. In some cases, the rate of oxygen delivery may be adjusted based on the determination by the processor.

Example 1

Figure 2:
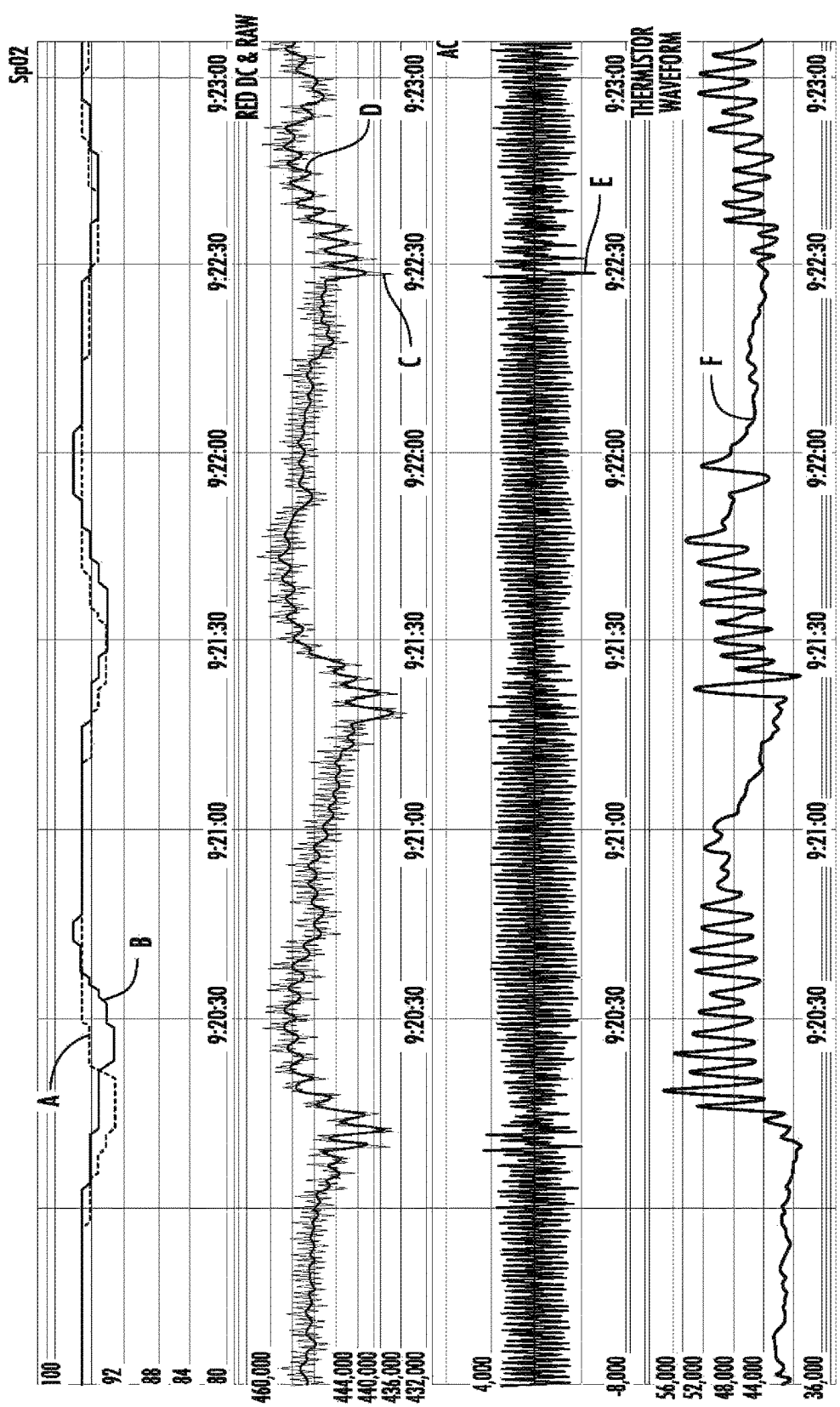
FIG. 2 provides PPG and thermistor data over time for a patient in the operating room who is having periods of obstructive apnea typical of obstructive sleep apnea. Signals "A" and "B" show the blood oxygen saturation (SpO2) over time obtained from a patient's nasal alar and finger, respectively. The signal "C" is the raw PPG signal, while signal "D" is the DC component of the PPG signal. Signal "E" is the AC component signal. Signal "F" is the thermistor signal (nasal air flow) over time.

FIGS. 1 and 2 show the PPG, thermistor and capnometry data streams for a patient in the operating room who is having periods of obstructive apnea typical of obstructive sleep apnea. The combination of the PPG data with the thermistor gives a reliable picture of respiratory status of the patient. In this case, the thermistor provides the most reliable data with patent airway and adequate tidal volume, and the PPG data is more reliable when patient is partially or completely obstructed (although the signal may work well most of the time and is not effected by obstruction or preferential nasal flow as may be the case with the thermistor) and amplitude is a fairly good measure of "effort". An "arousal" similar to OSA after the period of apnea may also be noted. Thus, PPG plus thermistor plus oximetry from the nasal ala allows a comprehensive picture of the respiratory status of the patient. As shown in FIG. 1, data from a capnograph may also be used with PPG either in combination with or in lieu of the thermistor.

We claim:

1. A method of determining the respiratory status of an individual, comprising securing to a central source site of the individual a device comprising a PPG sensor, and a secondary respiration sensor comprising a nasal air flow, nasal air pressure or exhaled $CO_2$ sensor, wherein the device is in communication with a signal processor;

monitoring changes in an amplitude of a PPG waveform from the PPG sensor via the signal processor, wherein the signal processor assigns an amplitude range centered around a zero crossing point to the PPG signal, and determines that a respiratory effort occurred within a time period when the amplitude of the PPG waveform crosses the PPG amplitude range twice in the time period;

monitoring changes in an amplitude of a waveform from the secondary respiration sensor via the signal processor, wherein the signal processor assigns an amplitude range centered around a zero crossing point to the secondary respiration sensor signal and determines that a ventilation occurred within the time period when the amplitude of the secondary respiration sensor waveform crosses the secondary respiration sensor amplitude range twice in the time period;

and if the signal processor determines that the respiratory effort and the ventilation occurred within the time period, the signal processor determines that a breath occurred in the time period and uses the breath to calculate a respiratory rate of the individual, and if the signal processor determines that a respiratory effort, a ventilation, or both, do not occur in the time period, then no breath from that time period is used to calculate the respiratory rate.

2. The method of claim 1, wherein the secondary respiration sensor is a thermistor.

3. The method of claim 1, wherein the secondary respiration sensor is a capnometer.

4. The method of claim 1, wherein at least one of the PPG amplitude range and the secondary respiration sensor amplitude range is a fixed amplitude range.

5. The method of claim 1, wherein at least one of the PPG amplitude range and the secondary respiration sensor amplitude range fluctuates over time.

6. The method of claim 5, wherein at least one of the PPG amplitude range and the secondary respiration sensor amplitude range is a percentage of the total signal amplitude.

* * * * *